United States Patent [19]

Hancock et al.

[11] E Re. 31,035

[45] Reissued Sep. 21, 1982

[54] ARRANGEMENT FOR PREPARING NATURAL TISSUE FOR IMPLANTATION

[75] Inventors: Warren D. Hancock, Newport Beach; Frederick P. Sattler, Fullerton, both of Calif.

[73] Assignee: Hancock Laboratories, Inc., Anaheim, Calif.

[21] Appl. No.: 922,654

[22] Filed: Jul. 7, 1978

Related U.S. Patent Documents

Reissue of:

[64] Patent No.: 4,050,893
Issued: Sep. 27, 1977
Appl. No.: 665,520
Filed: Mar. 10, 1976

U.S. Applications:

[63] Continuation of Ser. No. 490,686, Jul. 22, 1974, abandoned, which is a continuation-in-part of Ser. No. 324,217, Jan. 16, 1973, abandoned, which is a continuation of Ser. No. 28,630, Apr. 15, 1970, abandoned.

[51] Int. Cl.[3] ..... C14C 3/16

[52] U.S. Cl. ..... 8/94.11; 3/1; 3/1.2; 3/1.4; 128/1 R

[58] Field of Search ..... 8/94.11

[56] References Cited

U.S. PATENT DOCUMENTS

| | | | |
|---|---|---|---|
| 2,900,644 | 8/1959 | Rosenberg et al. | 3/1 |
| 3,966,401 | 6/1976 | Hancock et al. | 8/94.11 |
| 3,988,782 | 11/1976 | Dardick et al. | 3/1 |

FOREIGN PATENT DOCUMENTS

| | | |
|---|---|---|
| 1938275 | 10/1970 | Fed. Rep. of Germany . |
| 2241698 | 3/1973 | Fed. Rep. of Germany . |
| 2077641 | 5/1971 | France . |
| 2064151 | 7/1971 | France . |
| 2151092 | 4/1973 | France . |
| 1325667 | 8/1973 | United Kingdom . |

OTHER PUBLICATIONS

Carpentier, "J. Thoracic & Cardiovascular Surgery", vol. 58, No. 4, Oct. 1969, pp. 467–483.

Reed, "J. Thoracic & Cardiovascular Surgery, " vol. 57, No. 5, May 1969, pp. 663–668.

Weldon, "A Prosthetic Stented Aortic Homograft for Mitral Valve Replacement", J. of Surgical Research, vol. 6, No. 12, Dec. 1966, pp. 548–552.

Eckner, "Virchows Arch. Abt. A. Path. Anat.", 346, pp. 318–329, 1969.

Glagov, "Archives of Pathology", vol. 76, Dec. 1963, pp. 62–68.

Wood, "J. Thoracic & Cardiovascular Surgery", vol. 46, No. 3, Sep. 1963, pp. 379–385.

Rosenberg, "Surgical Forum", vol. 6, 1955, pp. 242–246.

Creech, "Surgery", Sep. 1954, pp. 431–444.

Peirce, "American J. of Surgery", Sep. 1949, pp. 314–323.

Wolinsky, "Circulation Research", vol. XIV, May 1964, pp. 400–413.

Braunwald et al., vol. XIII, Trans. Amer. Society of Artificial Organs, 1967, pp. 111–113.

Geha et al., J of Thoracic and Cardiovascular Surgery, vol. 54, No. 5, Nov. 1967, pp. 605–629.

*Primary Examiner*—Paul R. Michl

*Attorney, Agent, or Firm*—Gausewitz, Carr, Rothenberg & Edwards

[57] ABSTRACT

An arrangement for preparing natural tissue in the form of a heart valve, vessel or the like for implantation in which tanning fluid under pressure is applied to a portion of the tissue so as to cause said tissue to assume substantially its natural configuration, while additional tanning fluid is applied to the remainder of the tissue, said tanning fluid being so applied for a time sufficient to cause the tissue to become fixed, and, for vessels or the like, a guide may engage the tissue during fixation, whereby said tissue maintains substantially the configuration of the guide.

31 Claims, 9 Drawing Figures

FIG. 2.
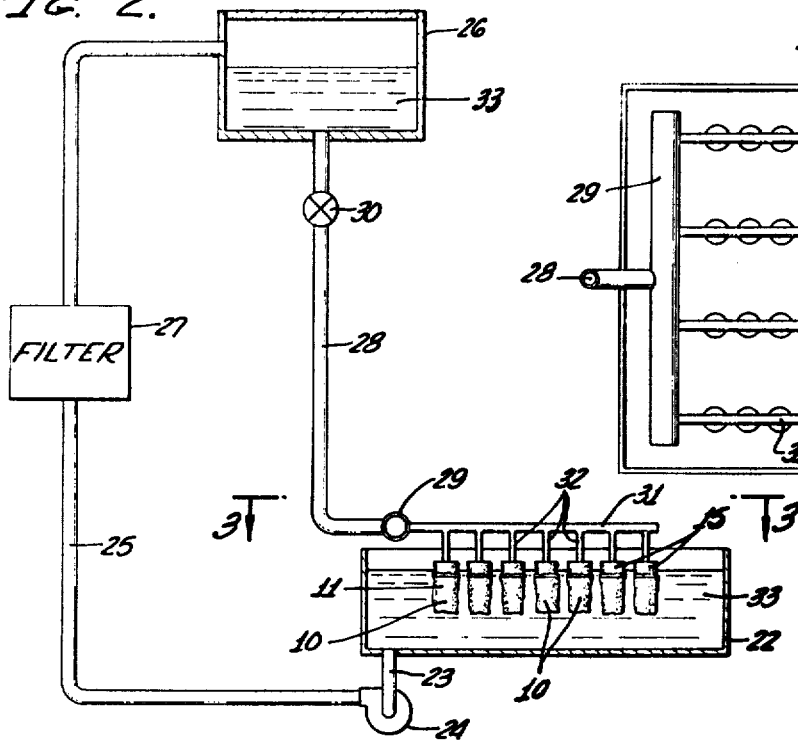
FIG. 3.
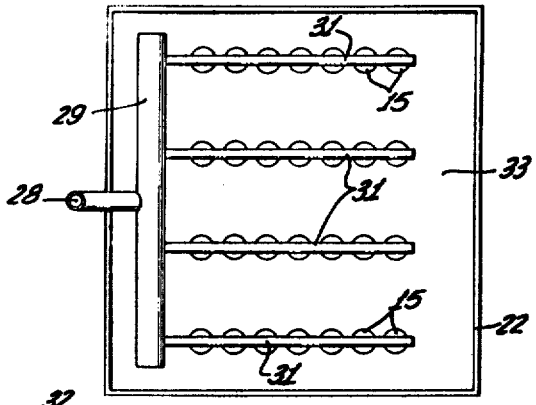
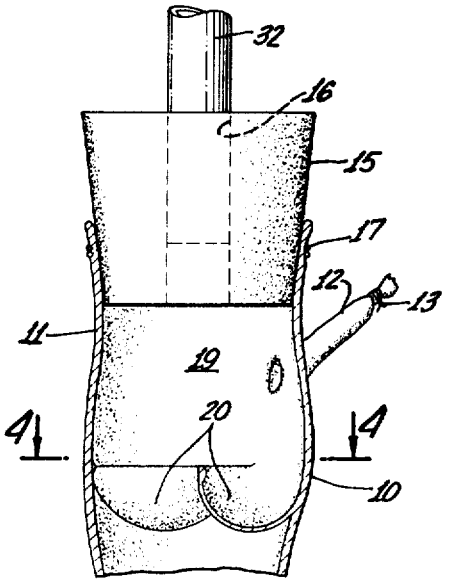
FIG. 1.
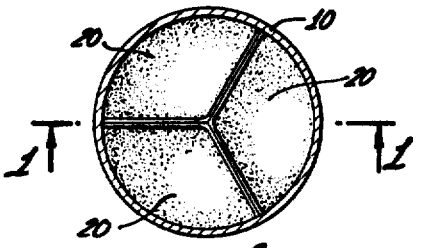
FIG. 4.
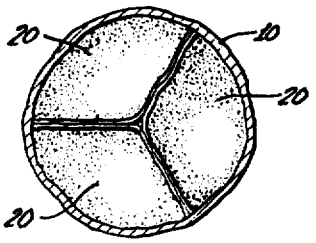
FIG. 5.

ARRANGEMENT FOR PREPARING NATURAL TISSUE FOR IMPLANTATION

Matter enclosed in heavy brackets [ ] appears in the original patent but forms no part of this reissue specification; matter printed in italics indicates the additions made by reissue.

REFERENCE TO RELATED APPLICATIONS

This is a continuation of patent application Ser. No. 490,686, filed July 22, 1974, now abandoned which is a continuation-in-part of our application Ser. No. 324,217 filed Jan. 16, 1973, now abandoned, which was a continuation of patent application Ser. No. 28,630, filed Apr. 15, 1970, now abandoned.

BACKGROUND OF THE INVENTION

1. Field of the Invention

This invention relates to the preparation of natural tissue for implantation.

2. Description of Prior Art

Natural aortic valves taken from animals or humans have been used for a number of years for allo and xenograft replacement of diseased valves. This has experienced only limited success, however, as in a large proportion of cases the replacement valves develop leakage. The incidence of incompetency has run from 40% to 80%. This occurs primarily because the valve is a very flexible and elastic structure which does not maintain its normal physiologic state when removed from the donor heart. This readily distortable element must then be matched with the flexible structure of the patient's heart, which also is not in its normal physiologic state when prepared for the valve replacement. With distortion of the flexible valve being unavoidable, and with no two valves being the same, it becomes virtually impossible to affix the valve to a stent or the patient's annulus at the proper location to maintain the valve's natural configuration. Consequently, undesirable stresses are introduced into the valve. This may result in immediate incompetence of the valve. Even where this does not prevent competence initially, the existence of the stresses in the valve over a period of time frequently causes premature failure.

If an appropriate tanning fluid is applied to a natural heart valve, its tissue becomes fixed so that it loses its characteristic of extreme flexibility and elasticity. As a result, in order to assure retention of approximately normal geometry, the cusps of the allo and xenograft valves have been packed with cotton, and the valves then have been fixed by tanning. This, however, has not solved the problem of valve failure because it never has been possible to impart exactly its natural configuration to a valve by packing it with cotton or similar material. Consequently, there are inevitably variations from the normal valve shape, and these differences become fixed in the valve by the tanning operation. These shape variations introduce stresses in the valve, which may cause it to fail subsequently.

Another problem encountered from such tanning of the valve is that shrinkage occurs as a result of this procedure. The amount of shrinkage is not the same in different valves, so that there is no way of predicting how much shrinkage will take place. Later, when the valve is exposed to biologic fluid after it has been implanted, it experiences some re-expansion. Again, this is an unknown amount. These factors contribute to the difficulty in properly mounting the valve and make the introduction of undesirable stresses practically unavoidable.

Similar problems have been encountered with vessels which also have been prepared for implantation by fixation with a tanning fluid. Problems have included inadequate penetration of the fixative, a lack of uniformity of fixation and insufficient tensile strength in the prepared vessels.

SUMMARY OF THE INVENTION

The present invention overcomes the difficulties previously encountered with natural valves, vessels and the like. It permits a natural heart valve to be fixed in its natural state so that it will retain its shape and can be readily and correctly mounted on a stent or affixed directly to the annulus of the heart of the patient. By this procedure, the valve is subjected to fluid pressure and at the same time fixed by exposure to a tanning fluid. It has been found that, when fluid pressure is applied to a valve after removal from the heart, the valve will be given its natural shape. Therefore, when fixed in a pressurized condition, the valve will retain its normal architecture, allowing proper mounting to be achieved. Similarly, vessels are subjects to pressure while being fixed with comparable improved results.

The valve may be pressurized by introducing the tanning fluid into it while subjecting the exterior of the valve to a bath of the same tanning fluid. In accomplishing this, the valve and associated ascending aorta are excised from the donor heart and attached to a stopper which has an opening through it. The tanning fluid is introduced through this opening into the interior of the valve, and a normal physiologic pressure is applied. This may be accomplished accurately by providing a source of the tanning fluid at a predetermined height with respect to the valve, so that the pressure head on the valve is at the correct value. After an appropriate period in the tanning solution, the valve is fixed in its natural contour and, upon removal, will retain this shape. Then, upon trimming, it is ready for mounting on a stent or for attachment to the heart of the patient. The prepared valve also may be stored frozen for future use or stored in the solution.

When fixed under pressure in this manner, the valve does not shrink during the tanning process, nor does undesirable expansion occur subsequently when the valve is subjected to the biologic fluid. The tanning process takes place more rapidly when the tanning solution is under pressure. Also, when tanned under pressure, the tensile strength of the tissue of the valve becomes increased. Improved results are obtained additionally because, when subjected to the pressure of the tanning fluid, valves that inherently will leak may be detected through the loss of fluid through the valve. These may be discarded to that only properly functioning valves will be retained for subsequent implantation.

In preparing a vessel, the collaterals and one end are ligated, and the other end is attached to a source of pressurized tanning fluid. While the interior of the vessel is subjected to the pressurized tanning fluid, the exterior is submersed in a bath of the tanning fluid. The natural overall contour of the vessel may be maintained as it is fixed by engaging it with a guide having the same general shape as the natural vessel contour. The guide also may impart a different contour to the vessel so that special shapes can be produced. The guide may be a rod received within the vessel or a tube surrounding the vessel.

BRIEF DESCRIPTION OF THE DRAWING

FIG. 1 is a longitudinal sectional view of a valve structure attached to a device for applying pressurized tanning fluid and after being fixed by the tanning fluid;

FIG. 2 is an elevational view, partially in section, illustrating an arrangement for treating a number of valves;

FIG. 3 is a top plan view showing the manifolding arrangement for distributing the tanning fluid;

FIG. 4 is a sectional view taken along line 4—4 of FIG. 1;

FIG. 5 is a view similar to FIG. 4 but illustrating the appearance of a valve in the absence of treatment in accordance with this invention;

DESCRIPTION OF THE PREFERRED EMBODIMENT

Figure 7:
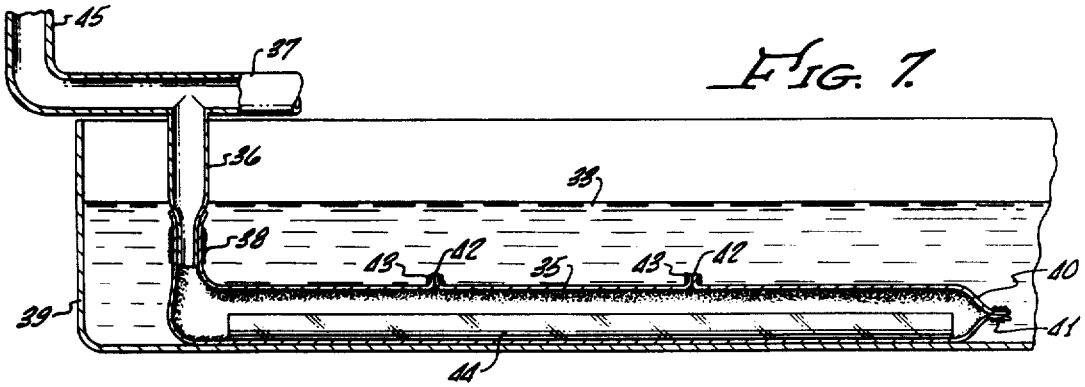
FIG. 7 is an enlarged fragmentary view of a portion of the arrangement of FIG. 6, the vessel being shown internally pressurized.

In preparation for a transplant, an aortic valve 10 is excised along with the ascending aorta 11 and extraneous tissue removed. This includes removal of the aorta above the sinus of the Valsalva, the annulus and subvalvular structure. The coronary arteries 12 are ligated by sutures 13. The aorta 11 then is extended around a rubber stopper 15, which has a central axially extending opening 16 through it. The stopper 15, therefore, is positioned in the aorta 11 above the valve 10, between the valve and the arch of the aorta. A suture 17 is wrapped around the exterior to affix the aorta to the stopper 15. The result is the formation of a chamber 19 within the valve structure, closed at its lower end by the cusps 20 of the valve. Access to the upper portion of the chamber 19 is provided by the opening 16 through the stopper 15. This allows pressurized tanning fluid to be introduced into the chamber 19 to fix the valve 10 in its natural configuration.

In order to pressurize the valve, the arrangement shown in FIGS. 2 and 3 may be employed, which provides a means for treating a number of valves simultaneously. This system includes an open-topped tank 22 from the bottom of which extends a line 23 to a pump 24. The latter, through a conduit 25, connects to a reservoir 26 that is located above the tank 22. A filter 27 in the line 25 will remove any impurities in fluid conducted through the line 25 to the reservoir 26. Extending downwardly from the reservoir 26 is a line 28, the lower end of which connects to a main manifold 29. A shutoff valve 30 may be included in the line 28. Additional and smaller manifolds 31 extend outwardly from the main manifold 29, each of these being provided with a plurality of downwardly extending stems 32. The openings 16 of stoppers 15 to which valve elements have been attached receive the open lower ends of the stems 32. This positions the valve structures 10 within the tank 22.

A suitable tanning fluid 33, such as formaldehyde, glutaraldehyde or other aldehyde, is introduced into the tank 22 and the reservoir 26. The fluid 33 in the tank 22 covers the exteriors of the valve structures 10. This causes the upstream ends of the valves 10 to be submerged in the tanning fluid 33.

The fluid 33 from the reservoir 26 fills the interior chambers 19 of the valves 10, where it is retained by the cusps 20. Because the reservoir 26 is elevated with respect to the location of the valves 10, a static pressure head is developed which causes the tanning fluid in the chambers 19 to exert pressure against each of the valves 10. This fluid pressure applied from the proximal aorta, being thus on the downstream side of the valve 10, inflates the valve and causes the valve to assume its natural contour. The maximum elevation of the fluid 33 in the reservoir 26 is kept at a height to produce a pressure head such that the valves will be pressurized within the physiologic range. This is from 80 to 120 mm Hg, with 80 mm Hg being used most frequently as the pressurizing value. The pressurization is controlled accurately and changed as needed by selecting an appropriate elevation of the reservoir 26 over the tank 22 to result in a desired pressure head. This pressure is maintained within the chambers 19 of the valve structures for a period sufficient to attain a fixation of the tissue of the valves. In a 4% formaldehyde solution or a 0.2% glutaraldehyde solution, this will occur in around 72 hours.

After being maintained under fluid pressure in the presence of the tanning fluid, the valve is removed and then may be handled without disturbing its natural geometry. It is then ready for mounting on a stent or for being affixed in the annulus of the heart of a patient. The natural shape of the valve may be maintained without difficulty as it is mounted, because any distortion is visually apparent. The valve will keep its shape when prepared in this manner, exhibiting neither shrinkage from the preparation nor expansion from subsequent contact with biologic fluid. The chance of incompetence, even after a prolonged period of subsequent use, is greatly reduced. The tissue of the valve achieves a higher tensile strength as a result of the tanning under pressure for greater life and assured performance. Furthermore, the process serves for quality control as valves exhibiting excess leakage can be detected and discarded. In the event that leakage past the cusps 20 of the valves 10 raises the level of the fluid 33 in the tank 22 too high, the excess is returned to the reservoir 26 by the pump 24.

In appearance, the prepared valve will resemble the illustration of FIG. 4 with a generally regular contour and coaptation of the cusps 20. The cusps are closed as in diastole, and the valve is in its normal physiologic state. Without the treatment in accordance with this invention, the valve may appear generally as shown in FIG. 5, with an uneven contour and the potential of leakage through the cusps.

Figure 6:
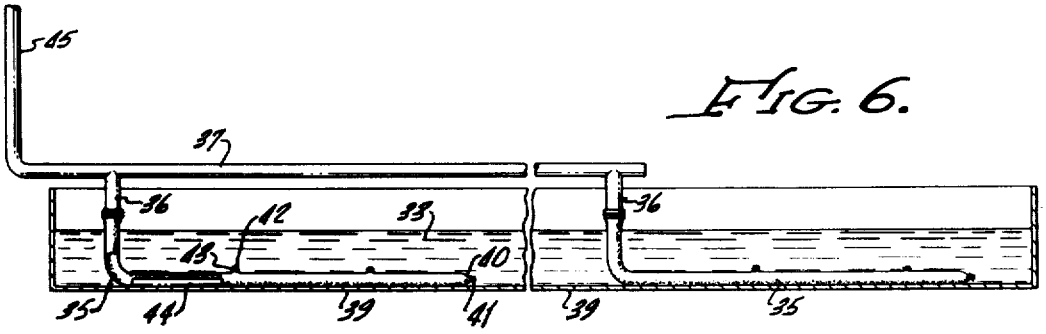
FIG. 6 is a side elevational view, partially in section, illustrating the arrangement for fixing vessels for implantation, utilizing straight rods for maintaining the configurations of the vessels.

The process of this invention as used in preparing arteries and veins for implantation may be seen in FIGS. 6 and 7. Here, one end of a vessel 35 is fitted over the downwardly extending stem 36 of a fluid manifold 37, held to it by means of sutures 38. The manifold 37 may be generally similar to the manifold 31 described above. The vessel 35 is received within a shallow tank 39 containing the tanning fluid 33. The other end 40 of the vessel 35 is ligated by sutures 41, and its collaterals 42 are ligated by sutures 43. This causes the vessel 35 to define an enclosed chamber. Within the interior of the vessel 35 is a straight rod 44, which extends the major part of the length of the vessel. The rod 44 is made of a suitable inert material, such as glass or a plastic such as polyolefin, and is of a constant outside diameter. The diameter of the rod 44 is less than that the vessel 35 assumes when it is under its normal physiologic pressure. The rod, however, serves to keep the vessel 35 straight under all conditions, this being the natural configuration for the vessel illustrated.

The manifold 37 is connected through a line 45 to an elevated reservoir of tanning fluid or other source of tanning fluid under pressure within the physiologic range. The internally applied tanning fluid inflates the vessel 35 so that during its period of fixation it assumes generally the normal diameter of a pressurized vessel. The tanning fluid in the tank 39 is applied to the exterior of the vessel 30 simultaneously to the internal pressurization with tanning fluid from the manifold 37. When treated in this manner, the vessel 35 has an improved shape, greater tensile strength and more uniformity of fixation with a greater penetration of the fixative than if conventional fixing procedures are followed.

Figure 8:
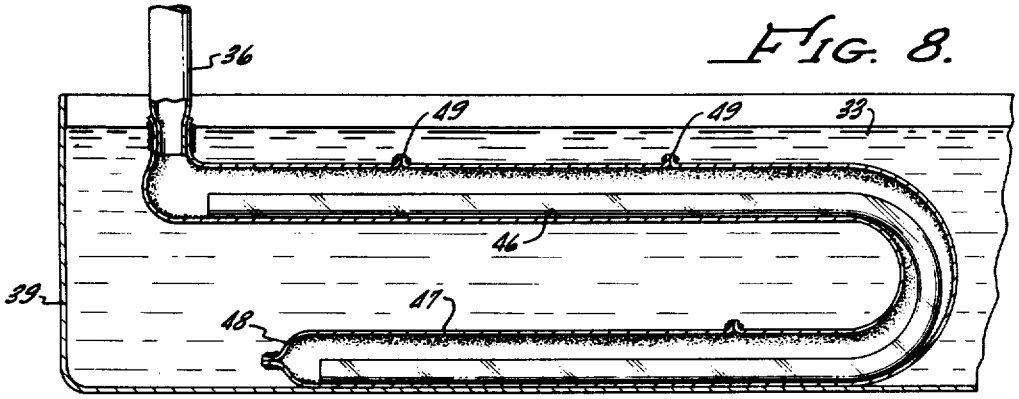
FIG. 8 is a view similar to FIG. 7 but of a vessel receiving a curved rod as a guide member, with the vessel shown pressurized.

The rod within the vessel need not be straight, but may be shaped to other contours to correspond to a desired overall configuration for the vessel. As shown in FIG. 8, the rod 46 is U-shaped, maintaining that contour for a vessel 47 which in its natural state has a different shape. Again, the end 48 of the vessel 47 is ligated as are its collaterals 49. The vessel is immersed in the tanning fluid 33 and attached to the manifold stem 36, as before. Pressure then is applied to the interior of the vessel during its period of fixation. When the tanning operation is complete, the vessel will retain substantially the U-shaped contour of the rod 46. This enables specially shaped natural vessels to be produced to suit particular requirements. The U-shaped vessel, for example, can be used as a shunt between vein and artery during kidney dialysis.

Figure 9:
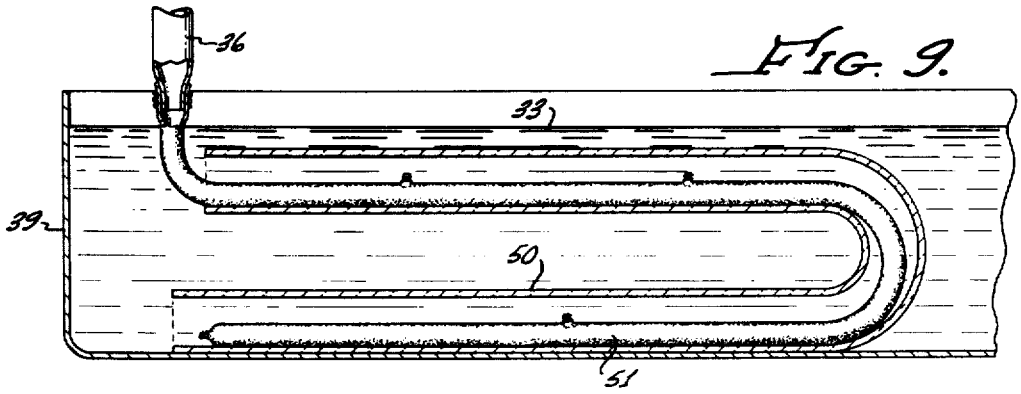
FIG. 9 is a view similar to FIGS. 7 and 8, but with a tube used to guide the vessel, and with the vessel shown unpressurized.

Instead of a rod within the vessel, a tube may be placed around the vessel to perform a similar function of maintaining it in a desired configuration. In FIG. 9 there is shown a U-shaped tube 50 of constant diameter surrounding a vessel 51, which has a natural shape differing from that of the tube. The tube 50 has a greater diameter than that of the vessel 51 before its interior is pressurized, as shown. However, pressurization of the vessel 51 will expand it to approach the lateral dimension of the tube 50. The tube 50 keeps the vessel 51 in the proper shape throughout the tanning process.

Other configurations of rod or tube may be devised to accommodate vessels to be fixed either in their natural shapes or in different shapes. Bifurcations, trifurcations and the like are possible utilizing a tube as the guiding element.

The foregoing detailed description is to be clearly understood as given by way of illustration and example only, the spirit and scope of this invention being limited solely by the appended claims.

We claim:

1. The method of preparing *a* natural heart valve for implantation *so that said valve will have improved tensile strength, will have and retain a generally regular contour with the cusps thereof closed as in diastole, and will be in substantially its natural configuration, so that said valve will remain competent for a prolonged period upon implantation,* comprising the steps of

*excising a heart valve from a donor heart,* applying a tanning fluid under pressure in the physiologic range to the downstream end of [a natural] *said* heart valve *so excised* so as to cause said valve to assume *a generally regular contour with the cusps thereof coapted and closed as in diastole so that said valve is in* substantially its natural configuration, and simultaneously applying a tanning fluid to the upstream end of said valve *and to substantially the entire exterior surface of said valve* at a pressure less than that at said downstream end, thereby to cause said valve substantially to maintain said configuration during *and after* fixation of the tissue thereof *so that said valve can remain competent for a prolonged period of use upon implantation.*

2. The method of preparing [a] *the* natural heart valve *of an animal* for implantation *in a patient so that said valve will have improved tensile strength, will have and retain a generally regular contour with the cusps thereof closed as in diastole, and will be in substantially its natural configuration, so that said valve will remain competent for a prolonged period of use upon implantation* comprising the steps of

*excising a heart valve from an animal heart,* applying a tanning fluid under pressure within the physiologic range to the downstream end of [a natural] *said* heart valve *so excised* so as to cause said valve to assume *a generally regular contour with the cusps thereof coapted and closed as in diastole so that said valve is in* substantially its natural configuration, applying said tanning fluid to the upstream end of said valve while said tanning fluid under pressure is so applied to said valve at the downstream end thereof so that said valve is at a higher pressure *from said tanning fluid* at said downstream end than at said upstream end,

[and] maintaining said tanning fluid so applied to said heart valve for a time sufficient to cause said valve to become fixed so as to substantially maintain said configuration *and to have improved tensile strength, whereby said valve can remain competent for a prolonged period of use upon implantation, and thereafter removing said valve so fixed from said tanning fluid and mounting said valve on a stent for subsequent implantation.*

3. The method as recited in claim 2 in which said pressure is substantially within the range of from about 80 to about 120 mm Hg.

4. The method as recited in claim 2 in which said tanning fluid is a 4% formaldehyde solution, and in which said tanning fluid is so applied to said valve for around 72 hours.

5. The method as recited in claim 2 in which said tanning fluid is a 0.2% glutaraldehyde solution, and in which said tanning fluid is so applied to said valve for around 72 hours.

6. The method as recited in claim 2 in which said tanning fluid under pressure is applied to said valve by maintaining a quantity of said tanning fluid so as to have a predetermined maximum height with respect to said valve, and connecting said quantity of tanning fluid to said valve so that said quantity of tanning fluid produces a pressure head applied to said valve.

7. The method of preparing a natural heart valve for implantation *so that said valve will have improved tensile*

*strength, will have and retain a generally regular contour with the cusps thereof closed as in diastole, and will be in substantially its natural configuration, so that said valve will remain competent for a prolonged period upon implantation,* comprising the steps of

*excising from a donor heart a unit that includes a heart valve and its ascending aorta, then* inserting *into said ascending aorta above said heart valve* a member having an aperture therethrough, [into the ascending aorta of a unit that includes a natural heart valve and its ascending aorta,]

attaching said aorta to said member so that said unit and said member define a chamber *closed at one end by the cusps of said heart valve* and said aperture provides access to the interior of said chamber at the downstream end of said valve, ligating the arteries of said unit so as to close said chamber, introducing a tanning fluid which is pressurized to within the physiologic range of pressure for said valve through said aperture into said chamber so as to inflate said valve and cause said valve to assume *a generally regular contour with the cusps thereof coapted and closed as in diastole so that said valve is* substantially its natural configuration, *with said tanning fluid being retained by said cusps of said heart valve,* applying such tanning fluid to the exterior of said unit *so that said tanning fluid engages substantially the entire exterior surface of said heart valve* while said pressurized tanning fluid is in said chamber with a greater fluid pressure existing in said chamber than on said exterior,

[and] maintaining said pressurized tanning fluid and said tanning fluid so applied to the exterior of said unit for a time sufficient to cause the tissue of said valve to become substantially fixed, thereby to cause said valve to substantially maintain said configuration *and to have improved tensile strength, and thereafter removing said valve so fixed from said tanning fluid and mounting said valve on a stent in preparation for implantation.*

8. The method as recited in claim 7 in which for introducing said pressurized fluid into said chamber a source of said tanning fluid is maintained at a predetermined height relative to said unit, and in which a conduit is extended from said source of said tanning fluid to said chamber to cause said tanning fluid at said source to provide a predetermined pressure head.

9. The method as recited in claim 8 in which said predetermined height is selected so as to provide a pressure head of around 80 mm Hg.

[10. The method of preparing for implantation natural tissues in a form in which a portion thereof is subjected to pressure within the physiologic range when implanted and which assumes a predetermined configuration as a result of such pressure comprising the steps of applying a tanning fluid to said portion of said tissues, said tanning fluid so applied being under pressure in the physiologic range so as to cause said tissues to assume substantially said predetermined configuration, and simultaneously applying a tanning fluid to remaining parts of said tissues at a pressure less than that of said portion of said tissues, thereby to cause said tissues to assume said configuration during fixation of said tissues.]

[11. The method as recited in claim 10 in which, for so applying said tanning fluid to said portion of said tissues with said tanning fluid being under pressure within the physiologic range, a source of said tanning fluid under pressure is provided, and a conduit is extended from said source to said portion of said tissues, for thereby so applying said tanning fluid to said portion of said tissues.]

[12. The method as recited in claim 11 in which, for said source of said tanning fluid under pressure, a quantity of said tanning fluid is provided at a predetermined height relative to said portion of said tissues.]

[13. The method of preparing a vessel for implantation comprising the steps of subjecting said vessel to a bath of tanning fluid so as to fix said vessel, and simultaneously engaging said vessel with a guide member of predetermined contour for causing said vessel to assume substantially said predetermined contour upon fixation thereof, said predetermined contour being different from the contour of said vessel in its natural state.]

[14. The method of preparing for implantation natural tissues in a form in which a portion thereof is subjected to pressure within the physiologic range when implanted and which assumes a predetermined configuration as a result of such pressure comprising the steps of applying a tanning fluid to said portion of said tissues, said tanning fluid so applied being under pressure within the physiologic range so as to cause said tissues to assume substantially said predetermined configuration, and applying a tanning fluid to remaining parts of said tissues while said tanning fluid under pressure is so applied to said portion of said tissues, so that said tissues experience a higher pressure at said portion thereof than at said remaining parts thereof.]

[15. The method as recited in claim 14 including the step of engaging said tissues with a guide member of predetermined contour while said tanning fluid under pressure within the physiologic range is so applied to said portion of said tissues for causing said tissues to assume substantially said predetermined contour.]

[16. The method as recited in claim 15 in which said tissues constitute a vessel.]

[17. The method as recited in claim 16 in which said vessel in its natural state has substantially said predetermined contour.]

[18. The method as recited in claim 16 in which said vessel in its natural state has a contour different from said predetermined contour.]

[19. The method as recited in claim 28 in which said predetermined contour is substantially U-shaped.]

[20. The method as recited in claim 16 in which, for said engaging of said vessel with a guide member, an elongated element having substantially said predetermined contour, and a lateral dimension less than that assumed by said vessel when subjected to pressure within the physiologic range, is inserted into said vessel for thereby maintaining said vessel substantially in said predetermined contour.]

[21. The method as recited in claim 16 in which, for said engaging of said vessel with a guide member, said vessel is placed within a tubular element having substantially said predetermined contour and an interior lateral dimension approximately that assumed by said vessel when subjected to pressure within the physiologic range, for thereby maintaining said vessel substantially in said predetermined contour.]

[22. The method as recited in claim 16 in which, for applying said pressure to said vessel, the end and any collaterals thereof are ligated, and said tanning fluid under pressure within said physiologic range is introduced into the interior of said vessel.]

[23. The method as recited in claim 22 in which, for introducing said tanning fluid under pressure within the physiologic range into said vessel, a source of said tanning fluid is maintained at a predetermined hight relative to said vessel, and a conduit is extended from said source of said tanning fluid to said vessel to cause said tanning fluid at said source to provide a predetermined pressure head.]

24. A *stent-mounted* natural heart valve for implantation having a generally regular contour, natural shape and size, coaptation of the cusps thereof and relatively high tensile strength prepared by the steps of

*excising a heart valve from a donor heart,* applying a tanning fluid under pressure in the physiologic range to the downstream end of [a natural] *said* heart valve *so excised* so as to cause said valve to assume substantially its natural configuration, and simultaneously applying a tanning fluid to the upstream end of said valve *and to substantially the entire exterior surface of said valve* at a pressure less than that at said downstream end, thereby to cause said valve substantially to maintain said configuration during fixation of the tissue thereof.

25. A *stent-mounted* natural heart valve for implantation having a generally regular contour, natural shape and size, coaptation of the cusps thereof and relatively high tensile strength prepared by the steps of

*excising a heart valve from an animal heart,* applying a tanning fluid under pressure within the physiologic range to the downstream end of [a natural] *said* heart valve *so excised* so as to cause said valve to assume substantially its natural configuration, applying said tanning fluid to the upstream end of said valve *so that said tanning fluid engages substantially the entire exterior surface of said valve* while said tanning fluid under pressure is so applied to said valve at the downstream end thereof so that said valve is at a higher pressure *from said tanning fluid* at said downstream end than at said upstream end, and maintaining said tanning fluid so applied to said heart valve for a time sufficient to cause said valve to become fixed so as to substantially maintain said configuration.

26. The heart valve as recited in claim 25 in which said pressure is substantially within the range of from about 80 to about 120 mm Hg.

27. The heart valve as recited in claim 25 in which said tanning fluid is a 4% formaldehyde solution, and in which said tanning fluid is so applied to said valve for around 72 hours.

28. The heart valve as recited in claim 25 in which said tanning fluid is a 0.2% glutaraldehyde solution, and in which said tanning fluid is so applied to said valve for around 72 hours.

29. The heart valve as recited in claim 25 in which said tanning fluid under pressure is applied to said valve by maintaining a quantity of said tanning fluid so as to have a predetermined maximum height with respect to said valve, and connecting said quantity of tanning fluid to said valve so that said quantity of tanning fluid produces a pressure head applied to said valve.

30. A *stent-mounted* natural heart valve for implantation having a generally regular contour, natural shape and size, coaptation of the cusps thereof and relatively high tensile strength prepared by the steps of

*excising from a donor heart a unit that includes a heart valve and its ascending aorta, then* inserting *into said ascending aorta above said heart valve* a member having an aperture therethrough, [into the ascending aorta of a unit that includes a natural heart valve and its ascending aorta,]

attaching said aorta to said member so that said unit and said member define a chamber *closed at one end by the cusps of said heart valve* and said aperture provides access to the interior of said chamber at the downstream end of said valve, ligating the arteries of said unit so as to close said chamber, introducing a tanning fluid which is pressurized to within the physiologic range of pressure for said valve through said aperture into said chamber so as to inflate said valve and cause said valve to assume substantially its natural configuration, *with said tanning fluid being retained by said cusps of said heart valve,* applying such tanning fluid to the exterior of said unit *so that said tanning fluid engages substantially the entire exterior surface of said heart valve* while said pressurized tanning fluid is in said chamber with a greater fluid pressure existing in said chamber than on said exterior, and maintaining said pressurized tanning fluid and said tanning fluid so applied to the exterior of said unit for a time sufficient to cause the tissue of said valve to become substantially fixed, thereby to cause said valve to substantially maintain said configuration.

31. The heart valve as recited in claim 30 in which for introducing said pressurized fluid into said chamber a source of said tanning fluid is maintained at a predetermined height relative to said unit, and in which a conduit is extended from said source of said tanning fluid to said chamber to cause said tanning fluid at said source to provide a predetermined pressure head.

32. The heart valve as recited in claim 31 in which said predetermined height is selected so as to provide a pressure head of around 80 mm Hg.

[33. Natural tissues for implantation and in a form in which a portion thereof is subjected to pressure within the physiologic range when implanted and which assumes a predetermined configuration as a result of such pressure, said tissues having full and uniform fixation and a relatively high tensile strength, and prepared by the steps of applying a tanning fluid to said portion of said tissues, said tanning fluid so applied being under pressure in the physiologic range so as to cause said tissues to assume substantially said predetermined configuration, and simultaneously applying a tanning fluid to remaining parts of said tissues at a pressure less than that of said portion of said tissues, thereby to cause said tissues to assume said configuration during fixation of said tissues.]

[34. The tissues as recited in claim 33 in which for so applying said tanning fluid to said portion of said tissues with said tanning fluid being under pressure within the physiologic range, a source of said tanning fluid under pressure is provided, and a conduit is extended from said source to said portion of said tissues, for thereby so applying said tanning fluid to said portion of said tissues.]

[35. The tissues as recited in claim 34 in which for said source of said tanning fluid under pressure, a quantity of said tanning fluid is provided at a predetermined height relative to said portion of said tissues.]

[36. A vessel for implantation having a contour different from the contour thereof in its natural state prepared by the steps of subjecting said vessel to a bath of tanning fluid so as to fix said vessel, and simultaneously engaging said vessel with a guide member of predetermined contour for causing said vessel to assume substantially said predetermined contour upon fixation thereof, said predetermined contour being different from the contour of said vessel in its natural state.]

[37. Natural tissues for implantation and in a form in which a portion thereof is subjected to pressure within the physiologic range when implanted and which assumes a predetermined configuration as a result of such pressure, said tissues having full and uniform fixation and a relatively high tensile strength, and prepared by the steps of applying a tanning fluid to said portion of said tissues, said tanning fluid so applied being under pressure within the physiologic range so as to cause said tissues to assume substantially said predetermined configuration, and applying a tanning fluid to remaining parts of said tissues while said tanning fluid under pressure is so applied to said portion of said tissues, so that said tissues experience a higher pressure at said portion thereof than at said remaining parts thereof.]

[38. The tissues as recited in claim 37 in which said preparation thereof includes the step of engaging said tissues with a guide member of predetermined contour while said tanning fluid under pressure within the physiologic range is so applied to said portion of said tissues for causing said tissues to assume substantially said predetermined contour.]

[39. The tissues as recited in claim 38 in which said tissues constitute a vessel.]

[40. The vessel as recited in claim 39 in which said vessel in its natural state has substantially said predetermined contour.]

[41. The vessel as recited in claim 39 in which said vessel in its natural state has a contour different from said predetermined contour.]

[42. The vessel as recited in claim 41 in which said predetermined contour is substantially U-shaped.]

[43. The vessel as recited in claim 39 in which for said engaging of said vessel with a guide member, an elongated element having substantially said predetermined contour, and a lateral dimension less than that assumed by said vessel when subjected to pressure within the physiologic range, is inserted into said vessel for thereby maintaining said vessel substantially in said predetermined contour.]

[44. The vessel as recited in claim 39 in which for said engaging of said vessel with a guide member, said vessel is placed within a tubular element having substantially said predetermined contour and an interior lateral dimension approximately that assumed by said vessel when subjected to pressure within the physiologic range, for thereby maintaining said vessel substantially in said predetermined contour.]

[45. The vessel as recited in claim 39 in which for applying said pressure to said vessel, the end and any collaterals thereof are ligated, and said tanning fluid under pressure within said physiologic range is introduced into the interior of said vessel.]

[46. The vessel as recited in claim 39 in which for introducing said tanning fluid under pressure within the physiologic range into said vessel, a source of said tanning fluid is maintained at a predetermined height relative to said vessel, and a conduit is extended from said source of said tanning fluid to said vessel to cause said tanning fluid at said source to provide a predetermined pressure head.]

*47. The method as recited in claim 2 in which, for so applying said tanning fluid to said upstream end of said valve, said valve is submersed in a bath of said tanning fluid.*

*48. The method as recited in claim 7 in which, for so applying said tanning fluid to the exterior of said unit, said unit is positioned in a bath of said tanning fluid so that said tanning fluid of said bath engages substantially the entire outer surface of said valve.*

*49. The method as recited in claim 7 in which,*

*for so applying said tanning fluid to the exterior of said unit, said unit is positioned in a tank containing said tanning fluid so that said tanning fluid of said tank engages substantially the entire outer surface of said heart valve,*

*and in which for so introducing said pressurized tanning fluid into said chamber*

*a reservoir containing said tanning fluid is maintained at a predetermined height above said unit,*

*and a conduit is extended from said reservoir to said aperture of said member to cause said tanning fluid of said reservoir to provide a predetermined pressure head within said chamber.*

*50. The method of simultaneously preparing a plurality of natural heart valves for implantation so that said valves will have improved tensile strength, will have and retain generally regular contours with their cusps closed as in diastole, and will be substantially in their natural configurations, so that said valves will remain competent for prolonged periods of use upon implantation comprising the steps of*

*excising from a plurality of donor hearts a plurality of units each of which includes a heart valve and its ascending aorta, then*

*inserting into each of said ascending aortas a member having an aperture therethrough, attaching said aorta of each of said units to the one of said members inserted therein so that said units and said members define chambers,*

*ligating the arteries of each of said units so as to close said chambers,*

*attaching said members to a manifold,*

*connecting a source of pressurized tanning fluid to said manifold so that said pressurized tanning fluid is introduced simultaneously into said chambers through said apertures of said members and exerts in said chambers a pressure which is within the physiologic range of pressure for said valves,*

*thereby to inflate said valves and cause them to assume generally regular contours with their cusps coapted and closed as in diastole so that said valves are in substantially their natural configuration with*

*said tanning fluid being retained in said chambers by the cusps of said heart valves,*

*positioning said manifold adjacent a tank containing a quantity of said tanning fluid so that said valves are submerged in said tanning fluid in said tank and said tanning fluid engages substantially the entire outer surfaces of said heart valves, while said source of pressurized tanning fluid is so attached to said manifold and exerts a greater fluid pressure in said chambers than on said outer surfaces of said valves,*

*and maintaining said source of pressurized tanning fluid so connected to said manifold and said manifold so positioned adjacent said tank for a time sufficient to cause the tissues of said valves to become substantially fixed,*

*thereby to cause said valves to substantially maintain said configurations and to have improved tensile strength.*

*51. The method as claimed in claim 50 including the steps of inspecting said valves while said source of pressurized tanning fluid is so connected to said manifold to detect loss of said pressurized tanning fluid through said valves, and discarding those of said valves through which there is an excessive loss of said pressurized tanning fluid.*

*52. In the method of replacing a diseased heart valve in a human patient with a natural tissue valve taken from an animal or a human wherein the natural tissue valve is fixed prior to implantation by exposure to a tanning fluid and thereafter mounted on a stent or affixed directly to the annulus of the heart of the patient, the improvement comprising*

*applying a tanning fluid under pressure in the physiologic range to the downstream end of said natural tissue valve so as to cause said valve to assume substantially its natural configuration,*

*and simultaneously applying a tanning fluid to the upstream end of said valve and to substantially the entire exterior surface of said valve at a pressure less than that at said downstream end,*

*thereby to cause said valve substantially to maintain said configuration during fixation of the tissue thereof.*

*53. In the method of replacing a diseased heart valve in a human patient with a natural tissue valve taken from an animal or a human wherein the natural tissue valve is fixed prior to implantation by exposure to a tanning fluid and thereafter mounted on a stent or affixed directly to the annulus of the heart of the patient, the improvement comprising*

*applying a tanning fluid under pressure within the physiologic range to the downstream end of said natural tissue valve so as to cause said valve to assume substantially its natural configuration,*

*applying said tanning fluid to the upstream end of said valve while said tanning fluid under pressure is so applied to said valve at the downstream end thereof so that said valve is at a higher pressure from said tanning fluid at said downstream end than at said upstream end,*

*and maintaining said tanning fluid so applied to said valve for a time sufficient to cause said valve to become fixed so as to substantially maintain said configuration.*

*54. The method as recited in claim 53 in which said pressure is substantially within the range of from about 80 to about 120 mm Hg.*

*55. The method as recited in claim 53 in which said tanning fluid under pressure is applied to said valve by maintaining a quantity of said tanning fluid so as to have a predetermined maximum height with respect to said valve, and connecting said quantity of tanning fluid to said valve so that said quantity of tanning fluid produces a pressure head applied to said valve.*

*56. The method as recited in claims 1, 2, 7, 53 or 54 in which said tanning fluid is a glutaraldehyde solution.*

*57. In the method of replacing a diseased heart valve in a human patient with a natural tissue valve taken from an animal or a human wherein the natural tissue valve is fixed prior to implantation by exposure to a tanning fluid and thereafter mounted on a stent or affixed directly to the annulus of the heart of the patient, the improvement comprising*

*excising from a donor heart a unit that includes a heart valve and its ascending aorta,*

*then inserting into said ascending aorta above said heart valve a member having an aperture therethrough,*

*attaching said aorta to said member so that said unit and said member define a chamber closed at one end by the cusps of said heart valve and said apertures provides access to the interior of said chamber at the downstream end of said valve, ligating the arteries of said unit so as to close said chamber, introducing a glutaraldehyde solution which is pressurized to substantially within the range of 80 mm Hg to 120 mm Hg pressure through said aperture into said chamber so as to inflate said valve and cause said valve to assume substantially its natural configuration, with said glutaraldehyde solution being retained by said cusps of said heart valve,*

*applying a glutaraldehyde solution to the exterior of said unit so that said glutaraldehyde solution engages substantially the entire exterior surface of said heart valve while said pressurized glutaraldehyde solution is in said chamber, with a greater fluid pressure existing in said chamber than on said exterior,*

*and maintaining said pressurized glutaraldehyde solution in said chamber and said glutaraldehyde solution so applied to the exterior of said unit for a time sufficient to cause the tissue of said valve to become substantially fixed,*

*thereby to cause said valve to substantially maintain said configuration.*

*58. The method as recited in claim 57 in which for introducing said glutaraldehyde solution into said chamber a source of said glutaraldehyde solution is maintained at a predetermined height relative to said unit, and in which a conduit is extended from said source of said glutaraldehyde solution to said chamber to cause said glutaraldehyde solution at said source to provide a predetermined pressure head.*

*59. The method as recited in claim 58 in which said predetermined height is selected so as to provide a pressure head of around 80 mm Hg.*

* * * * *